(12) United States Patent
Bose et al.

(10) Patent No.: US 7,063,707 B2
(45) Date of Patent: Jun. 20, 2006

(54) MEDICAL RETRIEVAL DEVICE

(75) Inventors: Arani Bose, Pelham, NY (US); David Barry, Fremon, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 274 days.

(21) Appl. No.: 10/382,760

(22) Filed: Mar. 6, 2003

(65) Prior Publication Data

US 2003/0212430 A1    Nov. 13, 2003

Related U.S. Application Data

(60) Provisional application No. 60/362,224, filed on Mar. 6, 2002.

(51) Int. Cl.
*A61B 17/22*    (2006.01)

(52) U.S. Cl. .................. 606/127; 606/198; 606/200

(58) Field of Classification Search ............... 606/194, 606/198, 200, 108, 110, 127
See application file for complete search history.

(56) References Cited

U.S. PATENT DOCUMENTS

| | | | |
|---|---|---|---|
| 4,505,767 A | 3/1985 | Quin | |
| 4,612,931 A | 9/1986 | Dormia | |
| 4,619,274 A | 10/1986 | Morrison | |
| 4,873,978 A | 10/1989 | Ginsburg | |
| 4,921,478 A | 5/1990 | Solano et al. | |
| 4,932,959 A | 6/1990 | Horzewski et al. | |
| 5,064,428 A | 11/1991 | Cope et al. | |
| 5,098,440 A | 3/1992 | Hillstead | |
| 5,171,233 A | 12/1992 | Amplatz et al. | |
| 5,190,546 A | 3/1993 | Jervis | |
| 5,370,647 A * | 12/1994 | Graber et al. ............... 606/127 |
| 5,474,563 A | 12/1995 | Myler et al. | |
| 5,496,330 A | 3/1996 | Bates et al. | |
| 5,630,822 A * | 5/1997 | Hermann et al. ........... 606/114 |
| 5,772,609 A | 6/1998 | Nguyen et al. | |
| 5,792,145 A | 8/1998 | Bates et al. | |
| 5,800,525 A | 9/1998 | Bachinski et al. | |
| 5,833,644 A | 11/1998 | Zadno-Azizi et al. | |
| 5,836,868 A | 11/1998 | Ressemann et al. | |
| 5,868,753 A | 2/1999 | Schatz | |
| 5,910,144 A | 6/1999 | Hayashi | |
| 5,938,645 A | 8/1999 | Gordon | |
| 5,944,728 A * | 8/1999 | Bates ........................ 606/127 |
| 5,989,266 A | 11/1999 | Foster | |
| 6,027,508 A | 2/2000 | Ren et al. | |

(Continued)

FOREIGN PATENT DOCUMENTS

DE    195 09 464    6/1996

(Continued)

OTHER PUBLICATIONS

U.S. Appl. No. 08/874,190, filed Jun. 13, 1997.

(Continued)

*Primary Examiner*—Glenn K. Dawson
*Assistant Examiner*—Michael Mendoza
(74) *Attorney, Agent, or Firm*—Crompton Seager & Tufte, LLC

(57) ABSTRACT

Alternative designs, materials and manufacturing methods for medical retrieval devices. Some embodiments pertain to a medical retrieval device including a cage having internal migration barriers therein. Some embodiments pertain to a medical retrieval device including a cage having variable diameters along the length thereof. Several alternative medical retrieval devices constructions and/or designs including methods and techniques of construction are also disclosed.

24 Claims, 9 Drawing Sheets

U.S. PATENT DOCUMENTS

| | | |
|---|---|---|
| 6,027,509 A | 2/2000 | Schatz et al. |
| 6,066,149 A | 5/2000 | Samson et al. |
| 6,077,298 A | 6/2000 | Tu et al. |
| 6,093,196 A | 7/2000 | Okada |
| 6,139,510 A | 10/2000 | Palermo |
| 6,159,220 A | 12/2000 | Gobron et al. |
| 6,171,327 B1 | 1/2001 | Daniel et al. |
| 6,187,016 B1 | 2/2001 | Hedges et al. |
| 6,190,394 B1 | 2/2001 | Lind et al. |
| 6,214,026 B1 | 4/2001 | Lepak et al. |
| 6,277,139 B1 | 8/2001 | Levinson et al. |
| 6,278,057 B1 | 8/2001 | Avellanet |
| 6,302,895 B1 | 10/2001 | Gobron et al. |
| 6,325,815 B1 * | 12/2001 | Kusleika et al. ............ 606/200 |
| 6,336,934 B1 * | 1/2002 | Gilson et al. ............... 606/200 |
| 6,361,545 B1 * | 3/2002 | Macoviak et al. .......... 606/200 |
| 6,383,205 B1 | 5/2002 | Samson et al. |
| 6,454,775 B1 | 9/2002 | Demarais et al. |
| 6,544,280 B1 | 4/2003 | Daniel et al. |

FOREIGN PATENT DOCUMENTS

| | | |
|---|---|---|
| WO | WO 96/01591 | 1/1996 |
| WO | WO 01/53559 | 7/2001 |

OTHER PUBLICATIONS

U.S. Appl. No. 09/715,878, filed Nov. 17, 2000.
U.S. Appl. No. 10/346,698, filed Jan. 17, 2003.

* cited by examiner

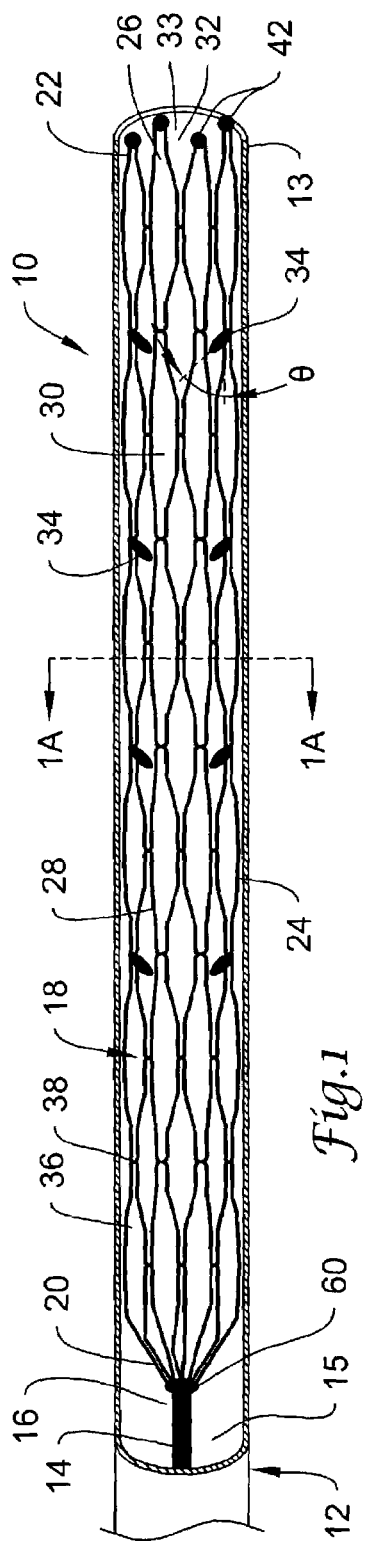
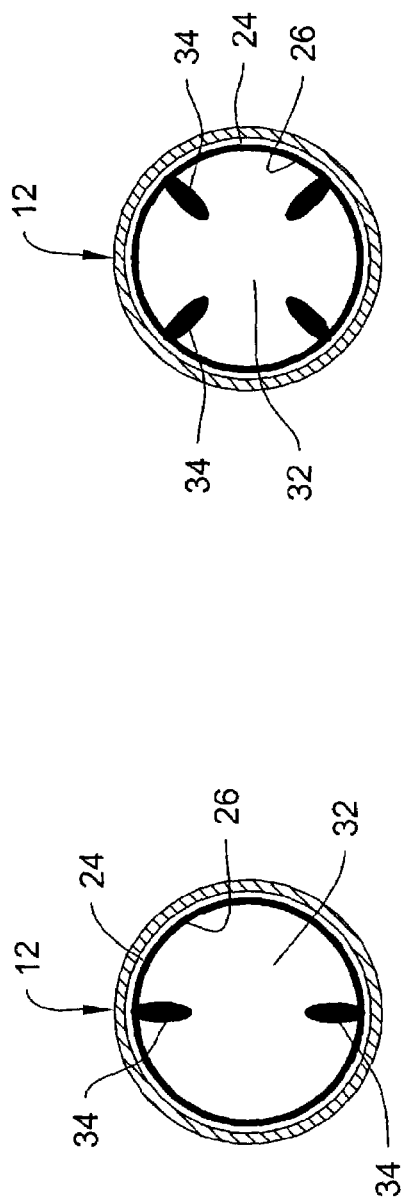
Fig.1
Fig.1A
Fig.1B

MEDICAL RETRIEVAL DEVICE

RELATED APPLICATIONS

This application claims priority to provisional patent application Ser. No. 60/362,224 filed Mar. 6, 2002, entitled "DEVICE FOR TREATMENT OF THROMBO-EMBOLIC STROKE", which is incorporated herein by reference.

FIELD OF TECHNOLOGY

The invention generally pertains to intracorporal medical devices, such as medical retrieval devices, or the like.

BACKGROUND

Thrombo-embolic stroke results when a piece of plaque breaks off from an artery (such as the carotid artery or a coronary artery), travels downstream, and becomes lodged in a smaller vessel in the brain. The piece of plaque (also known as clot) blocks blood flow to the region distal to the blockage. Absent blood flow, brain tissue will become compromised and eventually die. Ischemic stroke caused by thrombo-embolism is a leading cause of mortality and morbidity in the U.S. and around the world. In the U.S., approximately 800,000 people suffer thrombo-embolic stroke each year. The disease is the third leading cause of death and the leading cause of disability.

Therefore, there is an ongoing need to provide alternative designs, structures, assemblies, and/or treatment methods for retrieval and/or removal of a body, for example, a clot, an emboli, or a foreign body, from the anatomy of a patient, for example, the neuro-vasculature of a patient.

SUMMARY

The invention provides several alternative designs, structures, assemblies, treatment methods and/or methods of manufacturing medical devices adapted or configured for retrieval and/or removal of a body from the anatomy of a patient.

BRIEF DESCRIPTION OF THE DRAWINGS

The invention may be more completely understood in consideration of the following detailed description of various embodiments of the invention in connection with the accompanying drawings, in which:

FIG. 1 is a partial side view of a retrieval device in accordance with one example embodiment showing a cage member of the device in a first, unexpanded configuration within a delivery catheter, wherein a portion of the delivery catheter has been cut away to show the distal portion of the retrieval device;

FIG. 1A is a cross sectional view of the device of FIG. 1 taken along line 1A—1A of FIG. 1, and showing the internal migration barriers;

FIG. 1B is a cross sectional view of an alternative device similar of FIG. 1 showing an alternative configuration of internal migration barriers;

Figure 2:
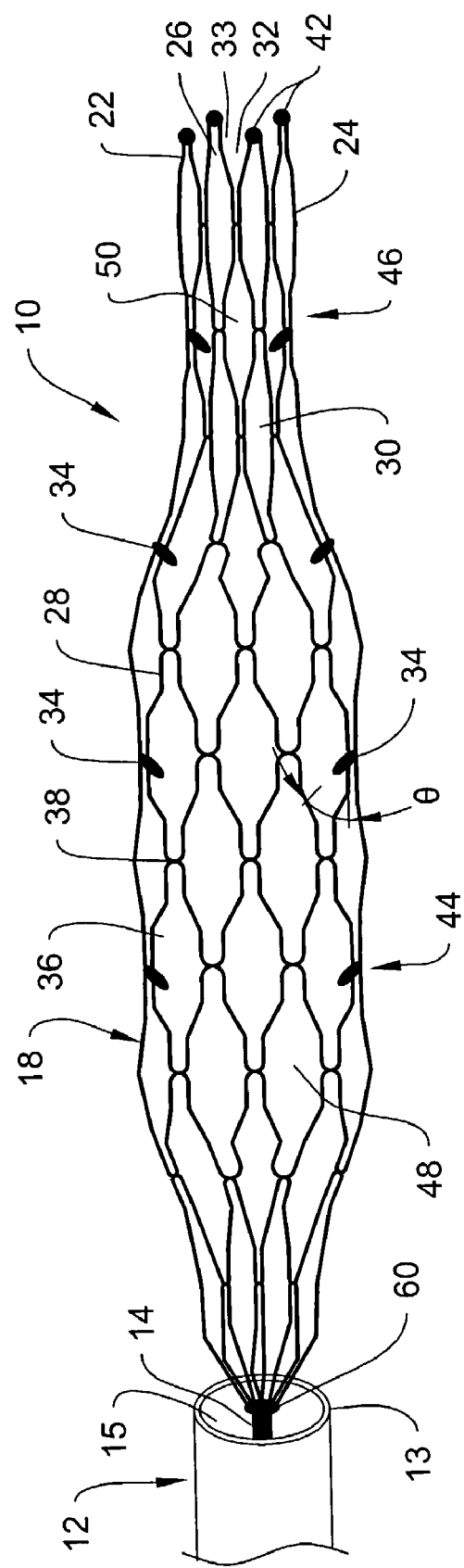
FIG. 2 is a partial side view of a retrieval device in accordance with the example embodiment of FIG. 1, showing the cage member of the device extending from the distal end of the delivery catheter and in a second, expanded configuration.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EXAMPLE EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. For example, although shown and discussed with specific reference to some embodiments which are adapted for use in removing bodies such as clots, emboli, or foreign bodies from the neuro-vasculature of a patient, it should be understood that the invention may be adapted or configured for use in other portions of the anatomy. For example, certain aspects of the invention may be applicable for use in other parts of the vasculature, or even in other parts of the anatomy.

Refer now to FIG. 1, which shows an example embodiment of a medical retrieval device 10 that includes a proximal shaft member 14 including a distal end 16, and a distal cage assembly or member 18 including a proximal end 20 and a distal end 22. The proximal end 20 of the cage member 18 is coupled to the distal end 16 of the shaft member 14.

In the embodiment shown, the cage member 18 can include a generally tubular structure having an exterior surface 24 and an inner surface 26 defined by one or more structures 28 defining interstitial spaces or apertures 30 there between. The inner surface 26 defines a lumen 32 extending within the generally tubular structure. A distal opening 33 into the lumen 32 is defined in the distal end 22 of the cage member. The cage member 18 includes one or more internal migration barriers 34 disposed on the inner surface 26 that extend into the lumen 32.

The structure of the cage member 18 is adapted or configured to be expandable from a first configuration, wherein the cage member 18 is sized for intracorporal insertion, for example, intravascular insertion, to a second, expanded configuration wherein at least a portion of the cage member 18 has a larger outer diameter than when in the first configuration. In FIG. 1, the device 10 is shown in an unexpanded first configuration within a sheath member, such as a delivery catheter 12, such as a microcatheter, or the like. In FIG. 2, the device 10 is shown such that the cage member 18 is extending from the distal end 13 of the delivery catheter 12, and the cage member 18 is shown in an expanded, second configuration. The expanding of the cage member 18 is accommodated by flexing and bending of the structural members that make up the generally tubular structure.

The structure, materials and/or dimensions of the cage member 18 are dictated primary by the desired characteristics and function of the device. It will be understood that a broad range of structure, materials and/or dimensions can be used. For example, in some embodiments, the cage member 18 can include one or more structures 28, or a lattice work or meshwork of one or more structures 28 such as ribbons, wires, filaments, struts, braids, helical members or coils, or other such structure to achieve the desired characteristics. In some example embodiments, the cage member 18 may take the form of a tubular coil, a tubular braid, a tubular structure made up of a framework of struts, a solid tubular member that has had portions removed there from, or other such structures. Additionally, although depicted as including a generally round cross-sectional shape, it can be appreciated that the tubular cage member 18 can include other cross-sectional shapes or combinations of shapes without departing from the spirit of the invention. For example, the cross-sectional shape of the generally tubular cage member 18 may be oval, rectangular, square, triangular, polygonal, and the like, or any other suitable shape, depending upon the desired characteristics.

In some example embodiments, the cage member 18 may resemble the design of a vascular stent. Many suitable stent configurations that are known may be used. For example, the cage member 18 may include of a series of cells 36 with interconnects 38 between the cells 36. The pattern of each cell 36 may be tailored to achieve the necessary combination of flexibility, structural integrity, and expansion ratio. In some other embodiments, the cage member or assembly 18 may include a plurality of expandable members or struts that are biased to expand in an outward direction when unconstrained radially, allowing the cage member 18 to expand when placed unconstrained within the anatomy of a patient. In some other embodiments, the structure of the cage member 18 can include wire-like members forming a distinct, repetitive serpentine pattern. This repetitive serpentine pattern can include multiple curves, for example U-shaped or D-shaped curves. The areas within the curves are open. With no recognizable beginning or end to this serpentine pattern, such wires form expandable serpentine elements. Serpentine elements can be arranged along the longitudinal axis of the cage member 18 so that the curves of abutting serpentine elements may be joined through an interconnecting element. Through the interconnecting elements, a continuous wire framework is created between multiple serpentine elements forming the cage member 18.

Some examples of suitable stent configurations that may be used for the cage member 18 are disclosed in U.S. patent application Ser. No. 08/874,190, filed Jun. 13, 1997, entitled "Polymeric Layered Stent", and in PCT Patent Application No. WO 0153559, and in U.S. patent application Ser. No. 09/715,878, filed on Nov. 17, 2000, entitled "Neurovascular Stent and Method", all three of which are incorporated herein by reference. In the latter patent application, in some example embodiments, the cells have an "inflection point" pattern. For example, refer to FIG. 9, and the related discussion below which shows one example embodiment of stent like structure that may be used in the cage member 18 in some example embodiments.

The skeletal framework of the cage member 18 may be formed through various methods as well, often depending upon the particular structure used. The framework may be formed by conventional construction methods. For example, individual structural members may be initially formed, shaped, bent, cut, wound, braided or the like, and coupled together in a desired configuration using suitable connection techniques, for example, welding, soldering, brazing, crimping, friction fitting, adhesive bonding, etc. For example, a wire element may be formed by shaping a wire segment and joining the wire ends to form the desired tubular member. In other embodiments, the framework may be formed from a single structural member that is formed or worked into a desired structure. For example, in some embodiments, the structure of the tubular member can be achieved by working or forming a thin-walled tube, for example, through laser cutting, micro-machining, chemically etching, or the like, to have the skeletal features making up the cage member 18. In the latter case, the structure of the cage member 18 is formed by cutting and removing portions of the tube.

In some embodiments, the openings or apertures 30 defined in the cage member can extend through the cage member 18 from the outer or exterior surface 24 to the inner surface 26 such that there is fluid communication between the lumen 32 and the exterior of the cage member 18. In some embodiments, the openings or apertures 30 can be sized such that when the cage member is in the second, or expanded configuration, the openings or apertures 30 are adapted to capture portions of the body, such as a clot, emboli, or foreign body, to be removed from the anatomy, while permitting the perfusion of blood through the vessel. For example, in some embodiments, at least some of the openings or apertures 30 are in the range of about 500 microns or greater in size. It should be understood that some other openings or apertures 30 in the cage member 18 can be larger or smaller than these example ranges.

As indicated above, the cage member 18 can include one or more internal migration barriers 34 that extend from the inner surface 26 into the lumen 32. The internal migration barriers 34 can be adapted and/or configured to engage, retain and/or reduce or prevent movement of portions of a body to be removed from the anatomy from within the lumen 32 of the cage member 18. For example, the internal migration barriers 34 can be adapted and/or configured to prevent the body from moving or slipping in a distal direction, or out of the distal end 22 of the cage member 18, for example, as it is withdrawn from the anatomy. Additionally, the internal migration barriers 34 can be adapted and/or configured to permit the body to enter into the lumen 32 of the cage member 18, for example, from a distal direction. Therefore, in some embodiments, the internal migration barriers 34 can be adapted and/or configured to allow for proximal movement of a body within the lumen 32, while reducing or preventing distal movement of the body within the lumen 32. The internal migration barriers 34 can be shaped, sized, angled, arranged, disposed, and/or be present in a number sufficient to achieve the desired function or result.

In some embodiments, the internal migration barriers 34 can take the form of barbs, spikes, protrusions, or the like, that are attached to, or are integrally formed with the structure of the cage member 18. The shape of the barriers 34 can be any shape suitable to achieve the desired function and characteristics. For example, the barriers 34 can be straight, tapered, curved, pointed, blunt, triangular, tooth like, hook like, knife like, or any other suitable shape. In some embodiments, the barriers 34 are generally straight barbs or spikes that are tapered to a pointed tip portion extending into the lumen 32.

In some embodiments, the individual barriers 34 can be angled inwardly and proximally within the cage member 18. For example, referring to FIGS. 1 and 2, an angle θ can be defined between an individual barrier 34 and the inner surface 26. In at least some cases, such angling can better enable a foreign body to be passed into the lumen 32 of the cage member 18, but provide a barrier or retainer to reduce or prevent the body from moving in a distal direction within the lumen 32. In some embodiments, at least some of the individual barriers 34 form an angle in the proximal direction relative to the inner surface 26 (for example, angle θ) that is in the range of about 10° to about 85°. It should be understood that some other individual barriers 34 in the cage member 18 can form larger or smaller angles in the proximal direction relative to the inner surface 26 than this example range.

The size of the individual barriers 34 can also vary, and be any suitable size to achieve the desired function and characteristics. The number of the individual barriers 34 can also vary, and again, may be any suitable number to achieve the desired function and characteristics. For example, some embodiments may not include any internal migration barriers, while other embodiment may include a large number of migration barriers.

The arrangement and/or placement and/or spacing and/or density of the migration barriers 34 along the length and/or about the circumference of the cage member 18 may also vary, depending upon the desired function and characteristics. For example, the migration barriers 34 may be arranged in a pattern along the length of the cage member 18, for example, such that they are spaced apart from one another along the longitudinal axis of the cage member 18. Such spacing can be consistent along the length of the cage member 18, or can vary. For example, the number or density of barriers 34 adjacent a distal portion of the cage member 18 may be high, while the number or density of barriers 34 adjacent a proximal portion of the cage member 18 may be relatively low, or vice versa. Additionally, the migration barriers 34 may be arranged in a pattern about the circumference of the cage member 18, for example, such that they are spaced apart from one another about the circumference of the cage member 18. Such spacing about the circumference can be consistent along the length of the cage member 18, or can vary. For example, refer now to FIG. 1A, which shows a cross section of the cage member 18, wherein there are two barriers 34 spaced opposite each other about the circumference of the cage member at a particular point along the length of the cage member 18. Refer also to FIG. 1B, which shows four barriers 34 spaced equidistant from each other about the circumference of the cage member 18 at a particular point along the length of the cage member 18. In other embodiments, additional or fewer barriers 34 can be arranged at a particular point along the length of the cage member 18. Collectively, these figures and this description illustrate that changes in the arrangement, number, density and/or configuration of barriers 34 along the length, and/or about the circumference of the cage member 18 may vary without departing from the scope of the invention.

The internal migration barriers 34 may be formed by conventional construction methods. For example, individual internal migration barriers 34 can be initially formed, shaped, bent, cut, or the like, and thereafter coupled in a desired configuration to the structure of the cage member 18 such that they extend from inner surface 26 into the lumen 32 in a desired manner. Suitable coupling or connection techniques include, for example, welding, soldering, brazing, crimping, friction fitting, adhesive bonding, and the like. In other embodiments, the individual internal migration barriers 34 may be formed in and/or integral with one or more of the individual structural members making up the cage member 18. In yet other embodiments, the individual internal migration barriers 34 may be formed along with the framework of the cage member 18 from a single structural member that is formed or worked into a desired structure including the internal migration barriers 34. For example, in some embodiments, the structure of the tubular member including internal migration barriers 34 can be achieved by working or forming a thin-walled tube, for example, through laser cutting, micro-machining, chemically etching, or the like, to have the skeletal features making up the cage member 18 and including the internal migration barriers 34. In the latter case, the structure of the cage member 18 and internal migration barriers 34 are formed by cutting and removing portions of the tube. The materials used to construct the internal migration barriers 34 can include any suitable material, for example, those discussed below with regard to materials used for the cage member 18, and can be the same or different material than those used to construct the cage member 18.

The shape of the cage member 18 can vary, depending upon the desired characteristics and function of the device 10. For example, when in the first, unexpanded, configuration, the shape of the cage member 18 can be adapted and/or configured to fit within the particular delivery device, such as catheter 12, being used. Referring to FIG. 1, in the embodiment shown, the cage member 18 can have a generally circular cross sectional shape that has a relatively constant outer diameter when in the first configuration. However, other shapes are contemplated, depending upon the delivery device used.

Figure 3:
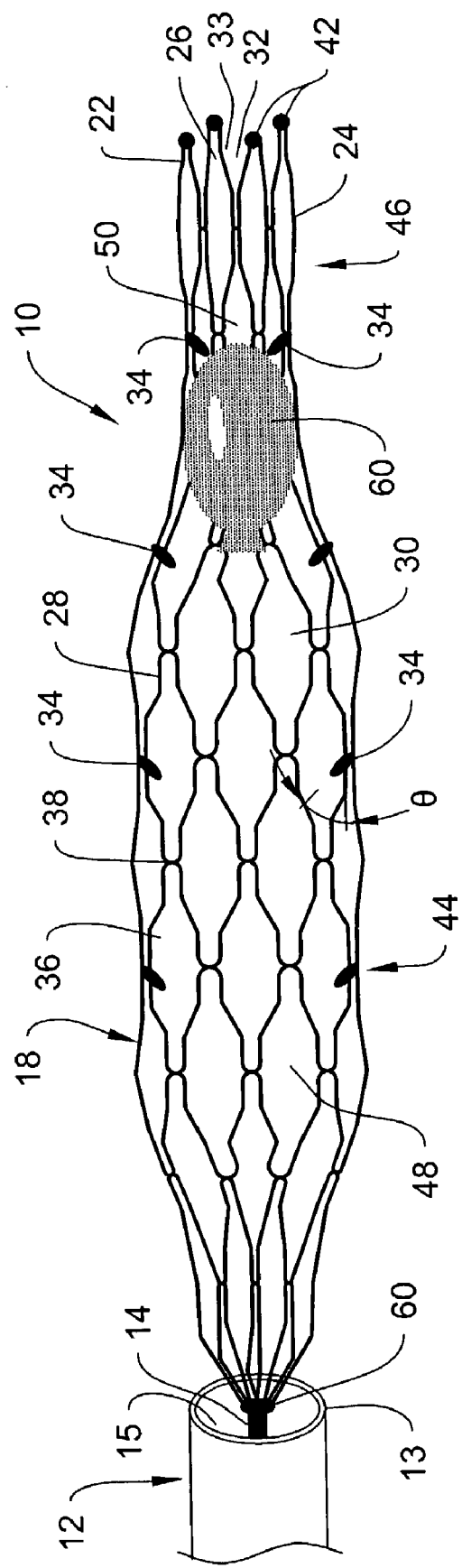
FIG. 3 is a partial side view of a retrieval device in accordance with the example embodiment of FIG. 2, showing a foreign body disposed within the lumen of the expanded cage member.

When in the second, expanded configuration, the cage member 18 can have the same, yet expanded, shape as it did in the first configuration, or can take on an alternative shape. For example, the cage member 18 in an expanded configuration may include different portions having different outer diameters that may be adapted and/or configured to enhance the function of the device. Refer now to FIG. 2, which shows the cage member 18 in an expanded configuration including a proximal portion 44 having a first outer diameter, and a distal portion 46 having a second, reduced outer diameter relative to the first outer diameter. This creates a "dual chamber" type cage, including a first chamber 48 within the proximal portion 44 and a second chamber 50 within the distal portion 46. In some embodiments, such an arrangement can be useful in preventing a body that is to be removed from the anatomy from slipping out of the cage 18 as it is withdrawn from the body. Additionally, such an arrangement can be useful in gripping and retaining different sized bodies that are to be removed from the anatomy. For example, refer now to FIG. 3, which shows the unconstrained device 10 after it has captured a foreign body 60, in this case a deflated detachable balloon. The foreign body could also be a blood clot or emboli or the like. The foreign body 60 has been captured in the distal portion 46 of the cage 18, although a larger object would pass into and be captured within the larger-diameter, proximal portion 44 of the cage 18. FIG. 3 also illustrates the internal migration barriers 34 blocking the object 60 from slipping out of the distal end of the cage 18, for example, as the device is withdrawn from the anatomy.

It should be understood that the illustrated shape is merely one example, and that in other embodiments, other arrangements or shapes can be used to achieve desired characteristics or functions. For example, more or fewer portions having a variety of outer diameters, and defining more or fewer chambers can be used.

The dimensions of the cage member 18 can be also be varied, for example, depending upon the anatomy in which the device is being used, the delivery device being used, the size or dimensions of the body (i.e. clot, emboli, or foreign body) being removed from the anatomy, and other such considerations. Obviously, at least some of the dimensions of the cage member will vary between the unexpanded first configuration and the expanded second configuration.

When the cage member 18 is in the first, unexpanded configuration, it is typically adapted and/or configured to fit within the delivery device being used. When the cage member 18 is in the second, expanded configuration, it may be designed in a variety of expanded diameters (e.g. to match the dimensions of the artery or body lumen, or to be adapted for the particular body being removed) and lengths (e.g. to match or be adapted to the dimensions of the clot or foreign body).

The cage member 18 may be made of any materials suitable for use, dependent upon the desired properties of the cage member. Some examples of suitable materials include metals, metal alloys, polymers, or the like, or combinations, mixtures, or composites thereof.

Some examples of suitable metals and metal alloys include stainless steel, such as 304V, 304L, and 316L stainless steel; nickel-titanium alloy such as a superelastic (i.e. pseudoelastic) nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it is desirable to use metals, or metal alloys that are suitable for metal joining techniques such as welding, soldering, brazing, crimping, friction fitting, adhesive bonding, etc.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Some examples of polymeric materials may include, but are not limited to: poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly (glycolide-co-trimethylene carbonate) (PGA/PTMC), polyethylene oxide (PEO), polydioxanone (PDS), polycaprolactone (PCL), polyhydroxylbutyrate (PHBT), poly (phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers, or mixtures or combinations thereof.

In at least some embodiments, it may be desirable that the cage member 18 exhibits a relatively high degree of biocompatibility since it is inserted in the body. Additionally, in some embodiments, it may be desirable that the cage member 18 have a relatively high degree of self expansion. Where the cage member 18 is self-expanding, some examples of suitable cage member 18 materials include compressible, biocompatible polymers, ELGILOY (available from Carpenter Technology Corporation of Reading, Pa.) and PHYNOX (available from Metallmphy of Imphy, France). Both of these metals are cobalt-based alloys which also include chromium, iron, nickel and molybdenum. Other materials for a self-expanding cage member 18 include 316 stainless steel and MP35N alloy which are available from Carpenter Technology Corporation and Latrobe Steel Company of Latrobe, Pa., and superelastic Nitinol nickel-titanium alloy which is available from Shape Memory Applications of Santa Clara, Calif. Nitinol alloy contains about 45% titanium. These materials are given by way of example only, and other suitable materials may be available.

In some embodiments, the cage member 18 can be formed of a shape-memory material, for example a shape memory alloy. In such embodiments, the shape memory effect can be used in the deployment of the cage member 18, for example in causing expansion of the cage member 18 from the first configuration to the second expanded configuration.

For example, in some embodiments, the cage member 18 can include or be made of a shape memory alloy that is martensite at room temperature, and has a final austenite transition temperature ($A_f$) somewhere in the temperature range between room temperature and body temperature. For example, in some such embodiments, the shape memory alloy has a final austentite transition temperature in the range of about 25° C. and about 37° C. (e.g. body temperature). In some such embodiments, it may be desirable that the final austentite transition temperature be at least slightly below body temperature, to ensure final transition at body temperature. This feature allows the cage member 18 to be carried in the sleeve member (such as a catheter) in a martensitic state, and assume its preformed, austenitic shape when expelled from the catheter and exposed to the higher body temperature at the target site. In this embodiment, deployment of the cage member 18 is achieved by a shape memory effect—as the material warms, it undergoes a transition from martensite to austenite form, causing expansion of the cage member 18 from the first configuration to the second configuration.

In other example embodiments, the cage member 18 can include or be made of a shape memory alloy that could have a transition temperature $M_d$ (wherein $M_d$=highest temperature to strain-induced martensite) that is in the range of body temperature (e.g. 37° C.) or greater, below which the alloy retains sufficient stress-induced martensitic property to allow placement of the cage member 18 at or above its final austentite transition temperature ($A_f$). In other words, this allows the cage member 18 to be carried in a sleeve 12 in a stress-induced martensitic (SIM) state, and recover its preformed, austenitic shape when released from the constraints of the catheter, at a temperature that may be substantially above the final austentite transition temperature without significant plastic, or otherwise permanent deformation. In this embodiment, the final austenite temperature may be quite low, e.g., 4° C. or lower, or it may be up to room temperature or higher.

In yet other embodiments, the cage member 18 can include or be made of a shape memory alloy that is martensite at body temperature, and has a final austentite transition temperature ($A_f$) somewhere in the temperature range above body temperature. This feature allows the cage member 18 to be carried in the sleeve member (such as a catheter) in a martensitic state, and maintain a martensitic state until exposed to a temperature higher than body temperature and expelled form the sleeve member 12. For example, in some such embodiments, the shape memory alloy has a final austentite transition temperature in the range of about 37° C. and about 45° C. In some such embodiments, it may be desirable that the final austentite transition temperature be at least slightly above body temperature, to ensure there is not final transition at body temperature. The cage member 18 can be heated to the necessary temperature above body temperature to make the transformation from martensite to austenite using an external heating means or mechanism. Such mechanisms may include the injection of heated fluid through the sleeve, the use of electrical or other energy to heat the cage member, or other such techniques.

Some examples or Nitinol cylindrical tubes having desired transition temperatures, as noted above, can be prepared according to known methods. In an exemplary method of manufacture of the cage member 18 having these properties, a nitinol hypotube, e.g., 8 mil wall thickness, is subjected to centerless grinding to a wall thickness of 3 mil. The cage member 18 pattern is cut by a laser (e.g., as described by Madou in Fundamentals of Microfabrication, CRC Press, 1997). Both inner and outer surfaces are polished to a mirror finish using electro-polish techniques (e.g., as described by Madou, 1997). The internal migration barriers 34, if any, can be formed integrally with, or attached to the inner surface. A gold coat may be applied by ion beam assist, or by sputtering. Alternatively, or additionally, a radio-opaque marker may be affixed to the cage member 18 to improve radio-opacity.

During manufacture, the cage member 18 is formed at the expanded condition (FIG. 2), corresponding to the final deployed size (e.g., about 3–8 mm outer diameter), and heated to a temperature above the transition temperature. The cage member 18 is then subjected to thermoelastic martensitic transformation (e.g., as described in U.S. Pat. No. 5,190,546 incorporated by reference in its entirety herein) by cooling below the transition temperature range of the alloy and deformation to the contracted condition suitable for use within an intraluminal catheter. The transition temperature can be modified by varying the ratios of each metal in the alloy and in one embodiment, is preferably is within the range between about 25° C. to 45° C. at which the cage member 18 expands. In some embodiments, the transition temperature range is between about 25° C. to 37° C. For example, the alloy can comprise 55% nickel, and 45% titanium which gives a transition temperature of about 32° C. to 33° C., which is below body temperature but above room temperature.

Nitinol cylindrical tubes having a martensite temperature $M_d$ below which the alloy can assume a stress-induced martensitic condition while being stressed to the extent necessary to place or otherwise use the device, of greater than about 37° C., or in some embodiments, greater than about 40° C., are also prepared according to known methods, e.g., U.S. Pat. No. 4,505,767. One example alloy would act, at about 37° C., as a constant force spring over a strain range up to about 5% or more. This is a measurement of the degree to which an alloy, at a given temperature, can be strained in a purely austentitic state by the formation of stress-induced martensite without significant plastic deformation. In other words, the strain caused by the application of a given stress at a given temperature is substantially recoverable. In practice, the maximum stress realized occurs sometime during the process of placing a nitinol device at a given temperature. Accordingly, a suitable alloy will provide a device that is capable of substantially recovering its austenitic shape without significant plastic deformation, upon placement of the cage member 18 in the body.

Additionally, as suggested above, in some embodiments, the cage member 18, or other portions of the device 10, can include portions thereof that may be doped with, coated or plated with, made of, or otherwise include a radiopaque marker material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like, or combinations or alloys thereof.

Referring to FIG. 1, marker members 42 are disposed adjacent the distal end of the cage member 18. The markers 42 may include or be made of radiopaque materials, as discussed above.

Further, the markers 42 shown may also act as atraumatic tip members disposed on the distal end of the cage member 18. In the embodiment shown, the radiopaque markers 42 are serving as both an imaging structure and as the atraumatic tip members. Such atraumatic members 42 may include a distal surface that is generally actuate or spherical in shape, and can help minimize the trauma to the anatomy, for example, an artery wall, as the device 10 is advanced distally to capture the body to be removed from the anatomy. In addition, such members may extend outward from the outer surface of the cage member such that they can slightly distend the anatomy, such as the artery wall, allowing the device 10 to slide more easily between the vessel wall and the body to be removed from the anatomy. It should also be understood that a wide variety of shapes and sized of such atramatic members can be used, and that in some embodiments, the atramatic members 42 do not necessarily need to be made of or include radiopaque material. The atramatic members 42 can be made of any suitable material, for example, metals, metal alloys, polymers, and the like.

As indicated above, the proximal end 20 of the cage member 18 is coupled to the distal end 16 of the shaft member 14. Any suitable attachment technique can be used, for example, friction fitting, mechanically fitting, chemically bonding, thermally bonding, welding (e.g., resistance, Rf, or laser welding), soldering, brazing, adhesive, crimping, or the use of a connector member or material, or the like, or combinations thereof. In the embodiments shown in FIGS. 1 and 2, the proximal end 20 of the cage member 18 is coupled to the distal end 16 of the shaft member 14 by crimping a band 60 disposed around and crimped to the junction of the shaft member 14 and the cage 18. In some embodiments, the band 60 may be made of, include, be plated, clad, or coated with, or otherwise include a radiopaque material as discussed above. Such a marker member may be useful in imaging the location of the proximal end of the cage 18.

Those of skill in the art and others will recognize that the materials, structure, and dimensions of the shaft member 14 are dictated primarily by the desired characteristics and function of the final device 10, and that any of a broad range of materials, structures, and dimensions can be used. For example, the shaft member 14 can include materials, structure, and dimensions that are in accordance with guidewire shaft constructions, such as microguidewire shaft constructions, generally known.

For example, the shaft member 14 may be formed of any materials suitable for use, dependent upon the desired properties of the shaft. Some examples of suitable materials include metals, metal alloys, polymers, or the like, or combinations or mixtures thereof. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable material, or combinations or alloys thereof. In some embodiments, it is desirable to use metals, or metal alloys that are suitable for metal joining techniques such as welding, soldering, brazing, crimping, friction fitting, adhesive bonding, etc.

In some embodiments, portions or all of the shaft member 14, or other structures included within the device 10, may be doped with, coated or plated with, made of, or otherwise include a radiopaque material, as discussed above in relation to the cage member 18.

The entire shaft member 14 can be made of the same material, or in some embodiments, can include portions or sections, for example, proximal/distal shaft sections, that are made of different materials. In some embodiments, the material used to construct different portions of the shaft can be chosen to impart varying flexibility and stiffness characteristics to different portions of the wire. For example, in some embodiments, a proximal section of the shaft may be formed of relatively stiff material such as straightened 304v stainless steel wire, and a distal shaft section may be formed of a relatively flexible material such as a straightened super elastic (i.e. pseudoelastic) or linear elastic alloy (e.g., nickel-titanium), or a alternatively, a polymer material, such as a high performance polymer. In general, if different materials are used for different sections of the shaft, the material used to construct a proximal portion is selected to be relatively stiff for pushability and torqueability, and the material used to construct distal portion 16 may be selected to be relatively flexible for trackability. However, alternative embodiments are contemplated.

Shaft member 14 can have a solid cross-section, but in some embodiments, can have a hollow cross-section. In yet other embodiments, shaft member 14 can include combinations of areas having solid cross-sections and hollow cross sections. Moreover, shaft member 14 can be made of rounded wire, flattened ribbon, or other such structures having various cross-sectional geometries. The cross-sectional geometries along the length of the shaft member can also be constant or can vary. For example, FIG. 1 depicts shaft member having a generally round cross-sectional shape. However, it can be appreciated that other cross-sectional shapes or combinations of shapes may be utilized. For example, the cross-sectional shape of shaft may be oval, rectangular, square, triangular, polygonal, and the like, or any suitable shape.

The shaft member 14 may include one or more tapers or tapered regions. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of the shaft section may be tapered and the taper can be in either the proximal or the distal direction.

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire during the grinding process. In some embodiments, the shaft member 14 can be centerless ground using a Royal Master HI-AC centerless grinder. Some examples of suitable grinding methods are disclosed in U.S. patent application Ser. No. 10/346,698 filed Jan. 17, 2003, which is herein incorporated by reference.

In some embodiments, the shaft member 14 may include an outer member, for example an outer polymer sleeve disposed about all or a portion of the shaft member 14.

Suitable material for use in such a sleeve can include any material that would give the desired strength, flexibility, lubricity, or other desired characteristics. Additionally, in some embodiments, a coating, for example a lubricious (e.g., hydrophilic) or other type of coating may be applied over portions or all of the medical devices or structures discussed above. For example, such a coating may be applied over portions or all of the device 10, including, for example, shaft member 14, band 60, the cage member or assembly 18, or other portions of the device 10. Hydrophobic coatings such as fluoropolymers, silicones, and the like provide a dry lubricity which improves device handling and device exchanges. Lubricious coatings improve steerability and can improve clot, emboli, or foreign body crossing capability. Suitable lubricious polymers are well known in the art and may include hydrophilic polymers such as, polyarylene oxides, polyvinylpyrolidones, polyvinylalcohols, hydroxy alkyl cellulosics, algirs, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions is coated with a fluoropolymer, such as polytetrafluroethylene (PTFE).

The length of the shaft 14 is typically dictated by the length and flexibility characteristics desired in the final medical device 10. For example, shaft section 14 can have a length such that when the cage member 18 is disposed about a body to be removed from a patient, a proximal end of the shaft extends out of the patient such that it can be manipulated by an operator.

The sleeve, or delivery catheter 12 can also be manufactured, include structure and/or size, or be made of materials so as to provide the desired characteristics. For example, the delivery catheter 12 can be made in accordance with many methods, structures, and arrangements as is generally known in the art. The delivery catheter 12 can be manufactured using structure and materials so as to maintain a desired level of flexibility and torquability appropriate for maneuvering the catheter as desired, for example, through the vasculature of a patient. In some embodiments, the catheter 12 can include a shaft that is generally characterized as having a tubular member construction that includes at least a single lumen 15 extending the length of shaft. At least the distal portion of the lumen 15 is adapted and/or configured to receive the device 10 when the cage member 18 is in a first, unexpanded configuration. Additionally, the outer diameter of the delivery catheter should be appropriately sized such that it can navigate within the designated anatomy to the target site. Additionally, the delivery catheter 12 typically has a length that is adapted and/or configured to extend from a point outside the anatomy of a patient to a point adjacent to a treatment site. In some embodiments, the length of the delivery catheter 12 is shorter than the length of the device 10, to allow an operator to manipulate the proximal end of the device 10 when it is disposed within the anatomy. The catheter 12 can be constructed of one or more layers, and may include reinforcing material or layers. The catheter can be manufactured from any suitable material to impart the desired characteristics. Examples of some suitable materials include polymers, metals, metal alloys, and the like, as is generally known in the art.

One example embodiment of a system in accordance with the invention includes a delivery catheter 12 and a device 10 including a cage member 18 as described above.

Some example methods of placement of the device 10, including the cage member 18, within the anatomy for use will now be described with reference to FIGS. 4–8. Some embodiments are particularly useful in treating targets located in tortuous and narrow vessels, for example in the neurovascular system, or in certain sites within the coronary vascular system, or in sites within the peripheral vascular system such as superficial femoral, popliteal, or renal arteries. The target site in some embodiments is a neurovascular site, such as site in the brain, which is accessible only via a tortuous vascular path, by which is meant a vascular path containing a plurality of bends or turns which may be greater than 90° turns, and/or involving vessels which are in the range of about 8 mm or less, and in some cases as small as 2–3 mm or less, in diameter. However, it is contemplated that the device 10 may be used in other target sites within the anatomy of a patient.

Figure 4:
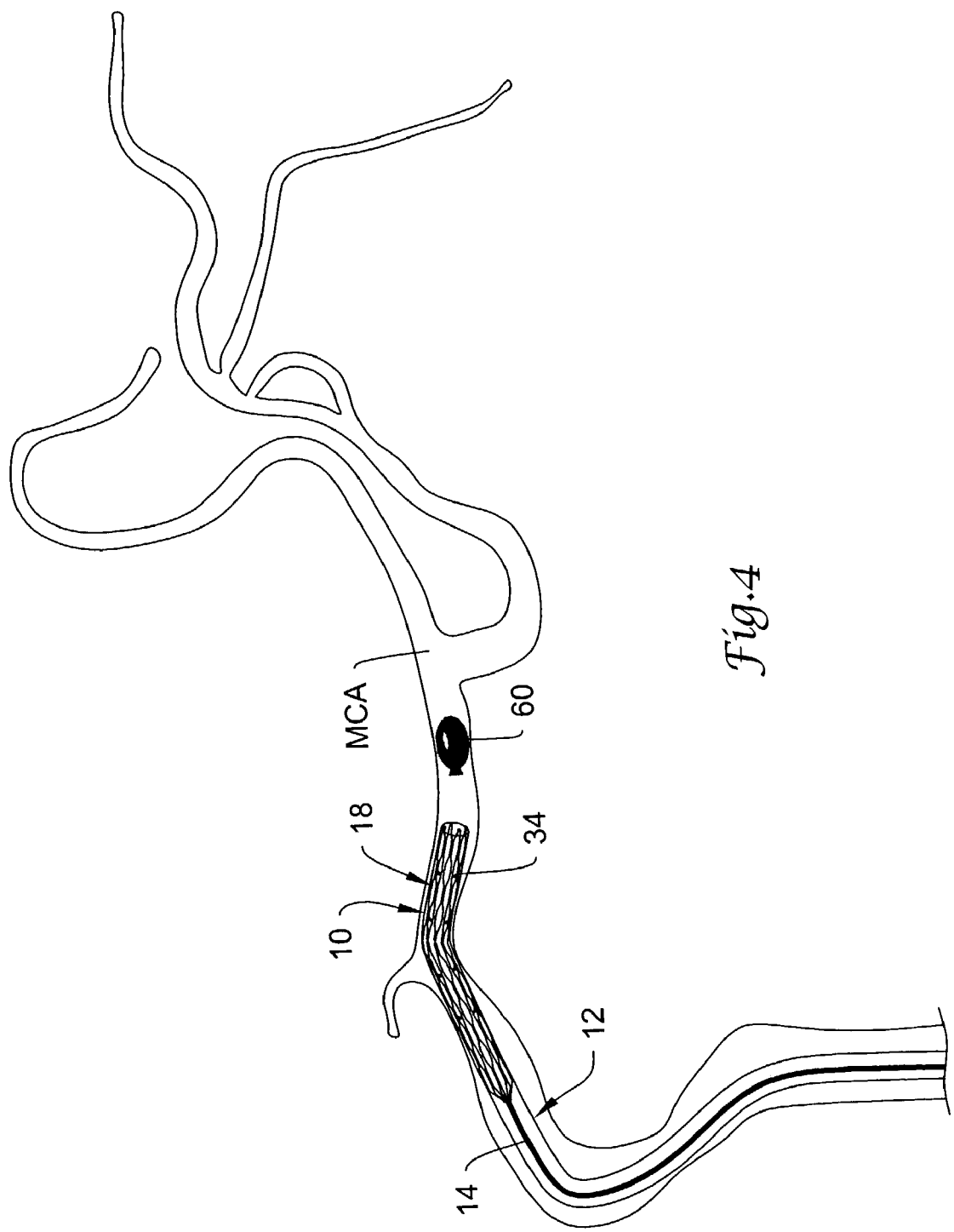
FIG. 4 is a partial cross sectional side view of the retrieval device in accordance with the example embodiment of FIG. 1, showing the device disposed within a delivery catheter in an unexpanded configuration, wherein the delivery catheter has been advanced within the anatomy of a patient to a site in the anatomy proximal of a foreign body that is to be removed from the anatomy.

For example, FIG. 4 shows a foreign object 60 lodged in within a vascular anatomy, for example, the Middle Cerebral Artery (MCA) in the brain. In this embodiment, the foreign object 60 is shown as a deflated detachable balloon, however, in other embodiments, other objects, such as a clot, emboli, or other foreign objects may be disposed in the anatomy. As shown in FIG. 4, the device 10 including the cage member 18 is constrained in the first, unexpanded configuration, within a microcatheter 12, and the micricatheter 12 has been advanced through the Internal Carotid Artery to a location proximal to the foreign body within the MCA. In some embodiments, a microcatheter 12 including the device 10 can be navigated directly to the target cite within the anatomy, as shown.

In other embodiments, a guidewire or guide catheter can be navigated to the target site according to known methods, and the microcatheter can be fed through or over the guidecatheter or guidewire as known. For example, the target site may be accessed by a flexible guidewire (such as described in U.S. Pat. No. 4,619,274) and a flexible guide catheter. Once the target site is reached, the guidewire can be pulled out, leaving the flexible guide catheter in place. The delivery catheter 12 can then be advanced within the guide catheter until the target site is reached. Other such permutations of using and exchanging devices, for example, guidewires and guide catheters, and the like, are generally known, and can be used to guide the microcatheter 12 including the device 10 to the target site.

Once the microcatheter 12 including the device 10 is appropriately located in a position proximal of the object 60 to be removed, the cage member 18 can then be deployed. Deployment can be achieved by pulling the microcatheter 12 in a distal direction while maintaining the position of the device 10 within the anatomy such that the cage member 18 extends out of the distal end of the microcatheter 12. In other embodiments, the cage member may be pushed out of the distal end of the catheter 12.

Figure 5:
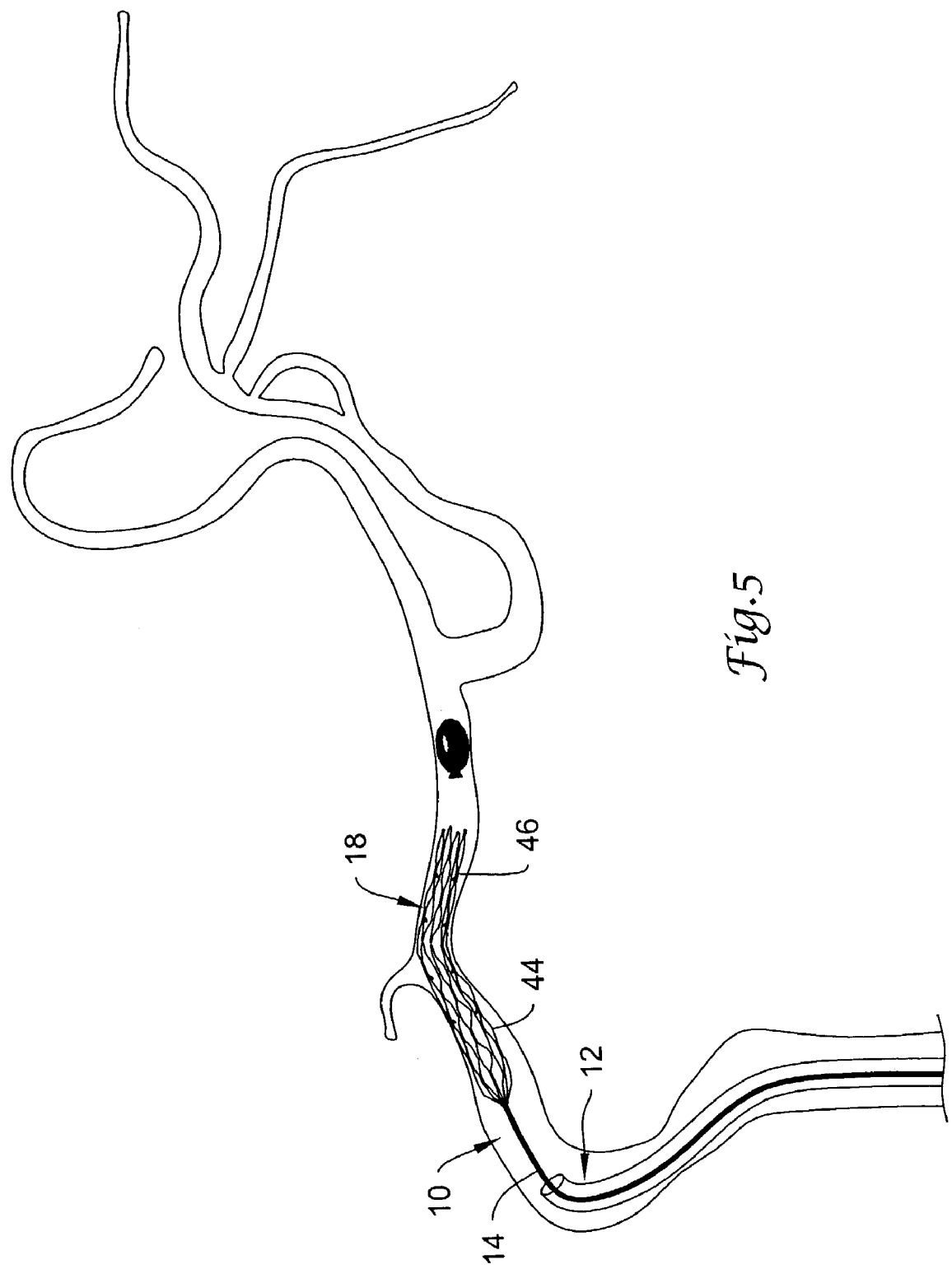
FIG. 5 is a partial cross sectional side view of the retrieval device in accordance with the example embodiment of FIG. 4, showing the delivery catheter being removed from the cage member of the device such that the cage member is in an expanded configuration within the anatomy.

FIG. 5 illustrates the device 10 after deployment of the cage member 18. Once the cage 18 has exited the distal tip of the microcatheter 12, it expands (such as through a shape memory effect) to the second configuration. In some embodiments, at least a portion of the cage member 18 can expand to oppose the vessel wall. The hourglass shape of the cage member 18, including proximal and distal portions 44/46, is also evident. The device 10 can then be advanced distally toward the foreign body 60.

Figure 6:
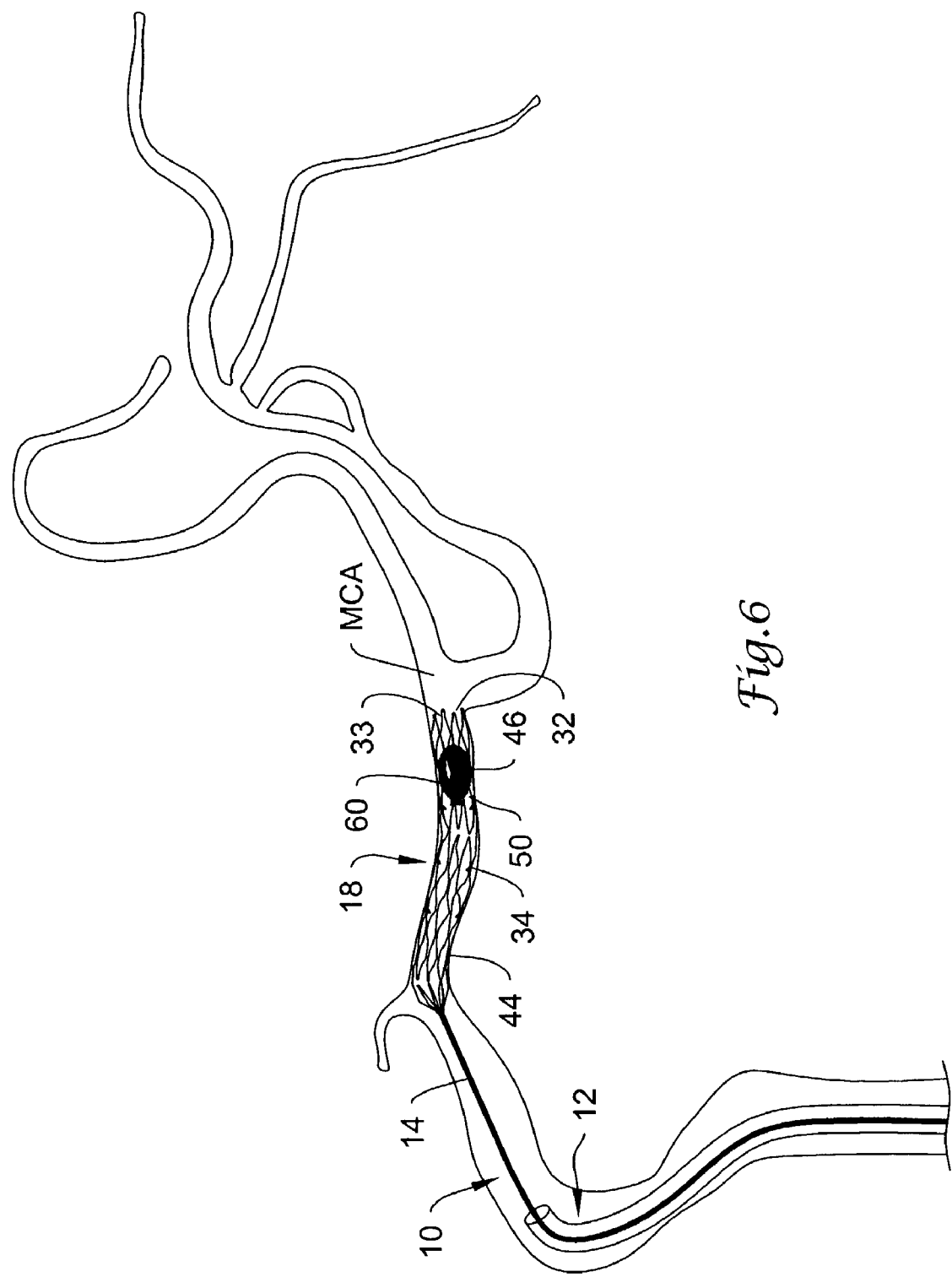
FIG. 6 is a partial cross sectional side view of the retrieval device in accordance with the example embodiment of FIG. 5, wherein the device has been advanced within the anatomy of a patient such that the distal portion of the cage member is advanced around the foreign body that is to be removed from the anatomy.

FIG. 6 illustrates the initial capture of the foreign body 60 by the cage member 18. The device 10 has been advanced distally such that the cage member 18 has extended or slipped between the vessel wall and the foreign body 60. The foreign body 60 enters the lumen 32 of the cage member 18 through the distal opening 33, and is captured in the smaller-diameter, distal chamber 50 of the cage 18.

Figure 7:
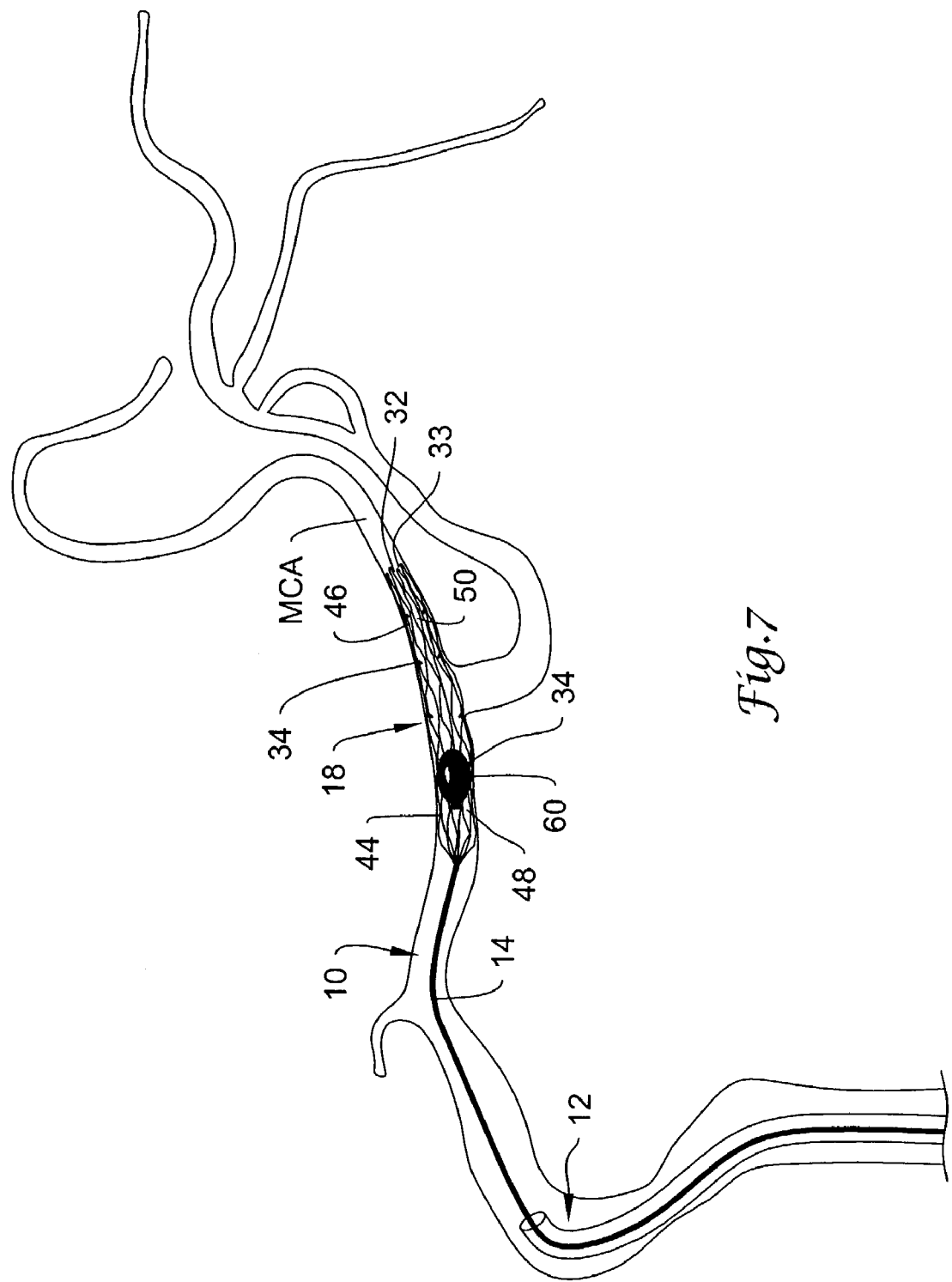
FIG. 7 is a partial cross sectional side view of the retrieval device in accordance with the example embodiment of FIG. 6, wherein the device has been further advanced within the anatomy of a patient such that the proximal portion of the cage member is advanced around the foreign body that is to be removed from the anatomy.

FIG. 7 illustrates the final capture of the foreign body 60. The device 10 is advanced further distally, such that the foreign body 60 is captured in the larger-diameter, proximal chamber 48 of the cage 18. The internal migration barriers 34 are angled proximally, and can act to prevent the foreign body 60 from slipping out of the cage 18 in a distal direction.

Figure 8:
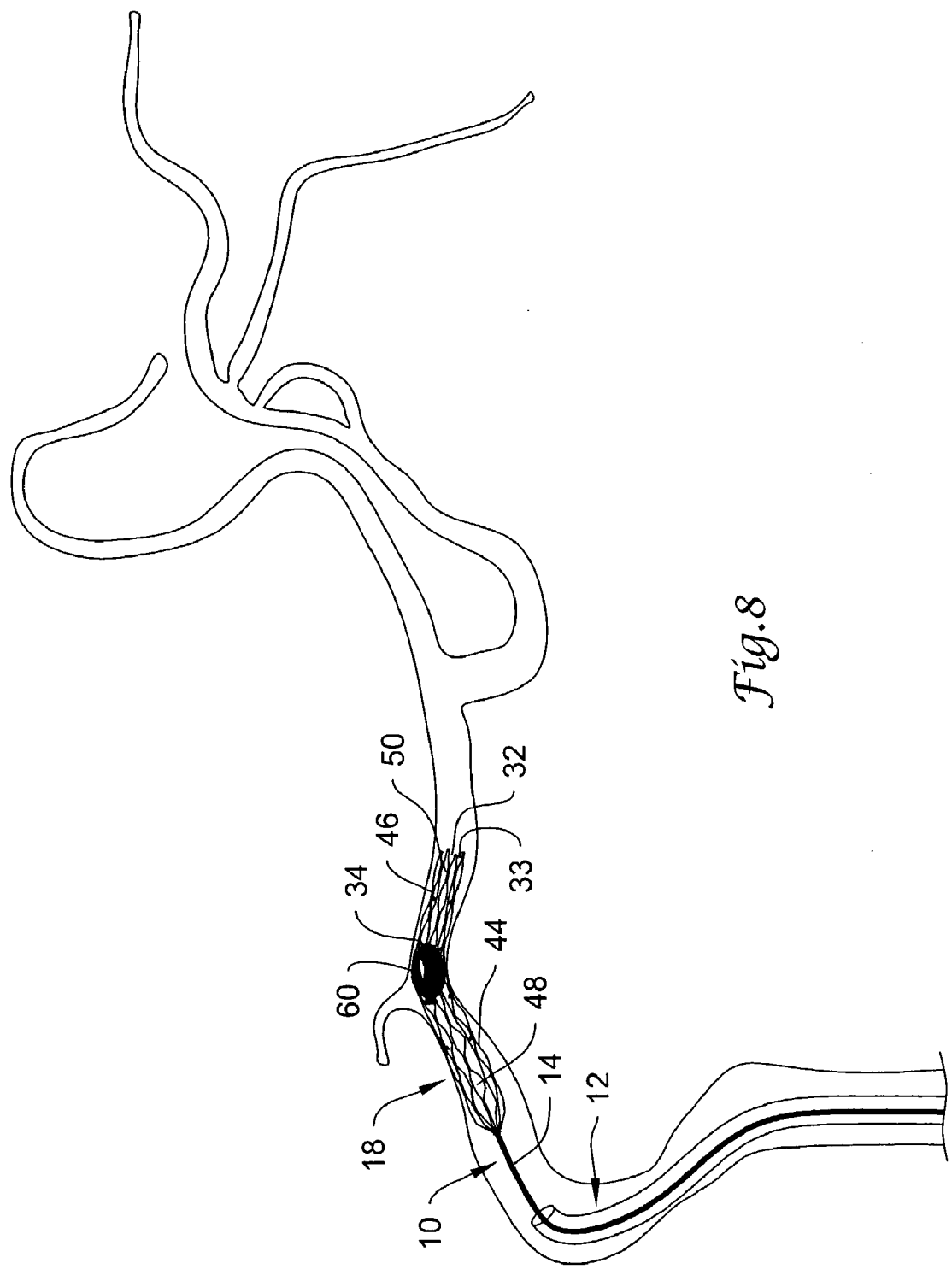
FIG. 8 is a partial cross sectional side view of the retrieval device in accordance with the example embodiment of FIG. 7, wherein the device has been pulled proximally within the anatomy showing the foreign body disposed within the cage member and in the process of being removed from the anatomy.

FIG. 8 illustrates the removal of the foreign body 60 from the patient. The device 10 is withdrawn proximally back through the Internal Carotid Artery. As the device 10 is withdrawn, the foreign body 60 is held in position inside the cage 18 by the internal migration barriers 34 and by the narrowing diameter shape between the proximal and distal chambers 48/50. To complete the procedure, the device 10, with the foreign body 60 captured, is withdrawn from the patient.

Figure 9:
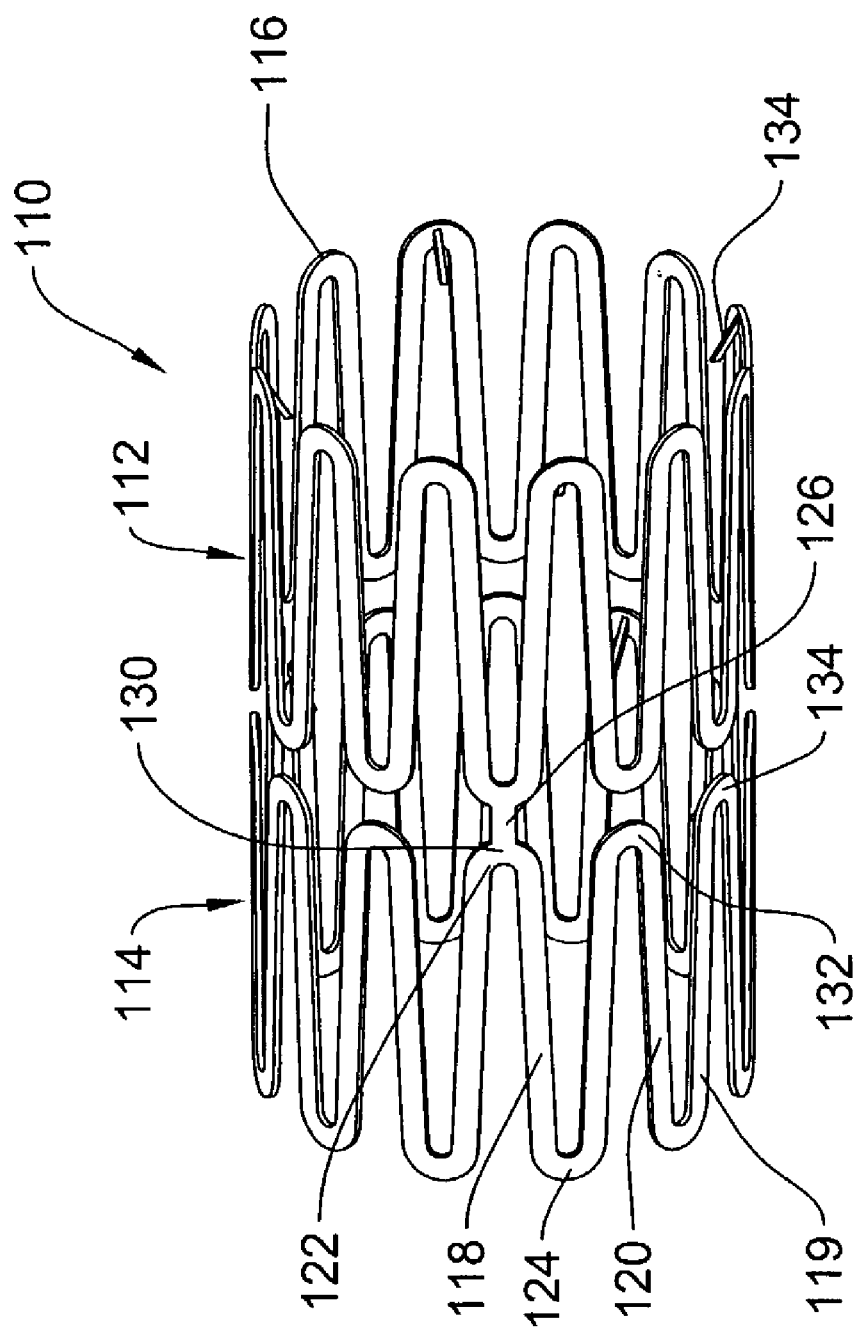
FIG. 9 is a partial side view of a portion of a cage member structure that can be used in some embodiments of the invention.

Refer now to FIG. 9, which shows one example embodiment of stent like structure that may be used to construct a cage member, for example cage member 18, for use in some embodiments of the invention. In this embodiment, the cage member 18, can include cage structure 110 that includes a plurality of expandable tubular members, such as tubular members 112, 114. In actual construction, the cage structure 110 may include many such members, e.g., 2–20, collectively forming an elongate cylindrical tube for use as a cage member, for example 18 as discussed above.

Each member of the cage structure 110 is formed of a continuous wire element, such as wire element 116 in member 112, forming a plurality of wave segments, such as wave segments 118, 120 in member 114, whose shape and expansion characteristics will be described further below. The wave segments have opposite looped peaks, such as looped peaks 122, 124 in wave segment 118.

Adjacent tubular members are connected one to another by axial connectors, such as axial connector 126 joining members 114, 116, and additional like connectors joining tubular members 112, or 114 members (not shown). As seen, the axial connectors connect confronting peaks in adjacent members, although connections to other pans of the wave segments is contemplated. In a typical cage structure 110, the connectors are spaced from one another by at least one; and preferably three or four unconnected confronting peaks. That is, a majority of the confronting peaks are unconnected, providing greater cage member flexibility in bending away from the cage member's long axis. Although the connectors shown here are simple linear connectors, the connectors may assume more complicated configurations, such as curved or zig-zag shapes which may themselves stretch to accommodate off-axis bending of the cage member, providing greater flexibility.

FIG. 9 shows portions of tubular members 112, 114, each formed of a continuous wire element, such as wire element 119 forming member 114. Each wire element, in turn, is formed of a series of repeating-unit wave segments, such as wave segments 118, 120, where the "end" of one segment is the "beginning" of the next segment.

The "end/beginning" point of the wave segments, which occurs at the same phase point in each wave, is arbitrary, and for purposes of illustration is indicated at a point, such as indicated at 130, 132, 134, which is near the top of the loop in the upper looped peak of each wave segment. Thus, wave segment 118 is defined as the portion of the wire element between points 130, 132, and segment 120, as the portion of the element between points 132, 134.

In the cage structures contracted state, the wave segments are compressed closely together where adjacent looped peaks are in contact with one another or nearly in contact, and the looped peaks are squeezed together. The wave segments forming the wire element can accommodate movement of the opposite arms of a wave segment, such as opposite arms 136, 138 in segment 118, away from one another, with relatively larger movement occurring in the center portion of the wave segment, i.e., the portion between opposite looped peaks. Internal migration barriers 134 can be disposed on the inner surface.

In some embodiments using the stent like configuration or cage structure 110 shown in FIG. 9 and discussed above, a cage member, for example cage member 18 discussed above, can include in the range of about 2 to about 20 tubular members, each tubular member being in the range of about 0.25 to about 1.0 mm in length. In some such embodiments, the axial connectors have a length typically in the range of about 3 to about 20% that of the tubular members. Each tubular member can include in the range of about 5 to about 25 wave segments, defined as repeating segments of the associated wire elements.

The characteristics of the wire-element shape, for example in the structures 110, can provide some advantages in a cage member intended for use in a small-diameter site. For example, in some embodiments, the cage member can be forced into a highly compressed or contracted state, with relatively little bending or stress in the peak regions. This contrasts with a saw-tooth wave, where much of the compression stress is concentrated at the peak points, and also with a regular sin wave that lacks the ability to be compressed tightly due to its relatively wide peak loops. Similarly, the stress on axially connected wire-element peaks that can occur when the cage member is bent away from its long axis (during movement through a tortuous vascular path) is distributed over the loop region, rather than being concentrated at a point. Both aspects can reduce the possibility of failure of the cage member by metal fatigue. At the same time, the cage member can undergo a several-fold radial expansion by virtue of the ability to be close packed in a contracted state (unlike a sin wave), and still provide significant expansion between wave segment arms. This is in contrast to a sin-wave wire element in which compression at the peaks, and thus the number of wave segments that can be accommodated in the contracted state, is limited. Additionally, in at least some embodiments, radial expansion of the cage member of such construction produces little change in the overall length of the tubular members, preserving the overall cage member length during deployment and expansion.

Such cage member structures 110 may be formed by conventional stent construction methods involving either initial formation of the individual tubular members, and subsequent attachment of one member to another by axial connectors, or by laser cutting a thin-walled tube to have the skeletal features making up the stent, as detailed above. In the former method, the wire element may be formed by shaping a wire segment and joining the wire ends to form the desired tubular member. In the latter case, the wire element is formed by cutting and removing portions of a cylindrical tube.

It should be understood that this disclosure is, in many respects, only illustrative. Changes may be made in details, particularly in matters of shape, size, and arrangement of steps without exceeding the scope of the invention. For example, alternative structure can be used in connecting the proximal and distal sections of guidewires. Additionally, alternative tip constructions including a flexible coil tip, a polymer jacket tip, a tip including a coiled safety/shaping wire, or combination thereof, and other such structure may be placed on the guidewire. The invention's scope is, of course, defined in the language in which the appended claims are expressed.

What is claimed is:

1. A medical retrieval device comprising:
   an elongated shaft including a distal end;
   a cage having a distal end and a proximal end, the proximal end of the cage coupled to the distal end of the shaft, the cage including an inner surface defining a lumen and at least one internal migration barrier,
   wherein the at least one internal migration barrier comprises an attached end and a free end, the attached end attached to an inside surface of the cage and the free end extending inwardly toward a longitudinal axis of the cage and proximally toward the proximal end of the cage.

2. The medical retrieval device of claim 1, wherein the cage includes a plurality of internal migration barriers extending from the inner surface of the cage into the lumen.

3. The medical retrieval device of claim 1, wherein the cage includes four or more internal migration barriers extending from the inner surface of the cage into the lumen.

4. The medical retrieval device of claim 1, wherein the cage comprises an elongated tubular member having a proximal end and a distal end, and the internal migration barrier is spaced from the distal end.

5. The medical retrieval device of claim 1, wherein the internal migration barrier is configured to contact a portion of a material entering the lumen of the cage to reduce the likelihood that such material will exit the distal end of the cage.

6. The medical retrieval device of claim 1, wherein the internal migration barrier forms an angle with the a plane of the inner surface that is in the range of about 10° to about 85°.

7. The medical retrieval device of claim 1, wherein the internal migration barrier is selected from a group consisting of a barb, a spike and a protrusion and is configured to contact a portion of a material entering into the lumen through the distal end of the cage to reduce the likelihood that the material will exit the lumen through the distal end of the cage.

8. The medical retrieval device of claim 1, wherein the cage includes a first portion having a first outer diameter, and a second portion having a second outer diameter, wherein the first outer diameter is larger than the second outer diameter.

9. The medical retrieval device of claim 8, wherein the first portion is a proximal portion and the second portion is a distal portion.

10. The medical retrieval device of claim 1, wherein the cage is adapted to be expandable from a first configuration sized for intracorporal insertion, to a second, expanded configuration, wherein at least a portion of the cage when in the second configuration has a larger outer diameter than when in the first configuration.

11. The medical retrieval device of claim 10, wherein when the cage is in the first configuration, it includes a portion having a generally constant outer diameter, and when the cage is in the second configuration, the portion expands such that it includes a first expanded region having a first outer diameter and a second expanded region having a second outer diameter different from the first expanded outer diameter.

12. The medical retrieval device of claim 11, wherein the first region is a proximal region and the second region is a distal region, and the proximal region has a greater outer diameter than the distal region.

13. The medical retrieval device of claim 10, wherein when the cage is in the first configuration, it is adapted for insertion into a neurovasculature of a patient.

14. The medical retrieval device of claim 1, wherein the cage comprises a shape memory material.

15. The medical retrieval device of claim 1, wherein the cage comprises an elongated tubular member comprising a single tubular structural member that is formed or worked into the desired structure.

16. The medical retrieval device of claim 1, wherein the cage includes a structure defining an exterior surface, the inner surface, and one or more interstitial spaces that extend through the structure from the exterior surface to the inner surface, wherein the spaces are in the range of about 500 microns or greater.

17. A medical retrieval device comprising:
   an elongated shaft including a distal end; and
   a tubular cage coupled to the distal end of the shaft, the cage adapted to be expandable from a first configuration sized for intracorporal insertion, to a second, expanded configuration wherein at least a portion of the cage has a larger outer diameter than when in the first configuration;
   wherein the tubular cage includes one or more internal migration barriers comprising an attached end and a free end, the attached end attached to an inside surface of the cage and the free end extending inwardly toward a longitudinal axis of the cage and proximally toward the proximal end of the cage; and
   wherein when the cage is in the first configuration, it includes a portion having a generally constant outer diameter, and when the cage is in the second configuration, the portion expands such that it includes a first expanded region having a first outer diameter and a second expanded region having a second outer diameter different from the first expanded outer diameter.

18. The medical retrieval device of claim 17, wherein the first region is a proximal region and the second region is a distal region, and the proximal region has a greater outer diameter than the distal region.

19. The medical retrieval device of claim 17, wherein the cage comprises a shape memory material.

20. The medical retrieval device of claim 19, wherein the cage expands from the first configuration to the second configuration through a shape memory effect.

21. A medical retrieval device comprising:
   an elongated shaft including a distal end;
   a tubular cage coupled to the distal end of the shaft, the cage including structure defining an exterior surface, an inner surface, and one or more interstitial spaces that extend through the structure from the exterior surface to the inner surface, wherein the spaces are in the range of about 500 microns or greater; and
   wherein the tubular cage includes one or more internal migration barriers comprising an attached end and a free end, the attached end attached to an inside surface of the cage and the free end extending inwardly toward a longitudinal axis of the cage and proximally toward the proximal end of the cage.

22. The medical retrieval device of claim 21, wherein the cage is adapted or configured to be expandable from a first configuration sized for intracorporal insertion, to a second, expanded configuration wherein at least a portion of the cage member has a larger outer diameter than when in the first configuration.

23. A method of making a medical retrieval device, the method comprising:

providing an elongated shaft including a distal end;

providing a cage having a distal end and a proximal end, the cage including an inner surface defining a lumen, the cage including at least one internal migration barrier extending from the inner surface of the cage into the lumen, the internal migration barrier comprising an attached end and a free end, the attached end attached to an inside surface of the cage and the free end extending inwardly toward a longitudinal axis of the cage and proximally toward the proximal end of the cage; and coupling the proximal end of the cage to the distal end of the shaft.

24. A method of removing a body from within the vasculature of a patient, the method comprising:

providing a medical retrieval device including:

an elongated shaft including a distal end;

a cage having a distal end and a proximal end, the proximal end of the cage coupled to the distal end of the shaft, the cage including an inner surface defining a lumen, the cage including at least one internal migration barrier extending from the inner surface of the cage into the lumen, the internal migration barrier comprising an attached end and a free end, the attached end attached to an inside surface of the cage and the free end extending inwardly toward a longitudinal axis of the cage and proximally toward the proximal end of the cage;

disposing the cage of the medical retrieval device within a delivery catheter;

advancing the delivery catheter to a site within the anatomy that is proximal to the body to be removed;

extending the cage of the medical retrieval device from within the delivery catheter;

advancing the cage of the medical retrieval device such that at least a portion of the body is disposed within the lumen; and removing the cage including the body from the anatomy of the patient.

* * * * *